United States Patent
Iida

(10) Patent No.: US 8,329,472 B2
(45) Date of Patent: Dec. 11, 2012

(54) GENE ASSOCIATED WITH FOAM FORMATION IN ACETIC ACID BACTERIUM, ACETIC ACID BACTERIUM MODIFIED TO REDUCE FOAM FORMATION, AND A METHOD FOR PRODUCING VINEGAR BY CULTURING AN ACETIC ACID BACTERIUM MODIFIED TO REDUCE FOAM FORMATION

(75) Inventor: Aya Iida, Handa (JP)

(73) Assignee: Mizkan Group Corporation (JP)

( * ) Notice: Subject to any disclaimer, the term of this patent is extended or adjusted under 35 U.S.C. 154(b) by 498 days.

(21) Appl. No.: 12/531,470

(22) PCT Filed: Mar. 13, 2008

(86) PCT No.: PCT/JP2008/000571
§ 371 (c)(1),
(2), (4) Date: Sep. 24, 2009

(87) PCT Pub. No.: WO2008/114497
PCT Pub. Date: Sep. 25, 2008

(65) Prior Publication Data
US 2010/0105117 A1    Apr. 29, 2010

(30) Foreign Application Priority Data
Mar. 20, 2007 (JP) .................... 2007-073498

(51) Int. Cl.
*C12N 15/00* (2006.01)
*C12N 1/21* (2006.01)
*C12N 9/10* (2006.01)

(52) U.S. Cl. ................ 435/440; 435/252.3; 435/320.1; 435/193

(58) Field of Classification Search ............ 435/193, 435/440, 69.1, 320.1; 536/23.2
See application file for complete search history.

(56) References Cited

OTHER PUBLICATIONS

Fuqua et al., Nature Reviews Molecular Cell Biology 3:685-695, 2002.*
Branden et al., Introduction to Protein Structure, Garland Publishing Inc., New York, p. 247, 1991.*
Seffernick et al. (J. Bacteriol. 183(8):2405-2410, 2001).*
Witkowski et al., Biochemistry 38:11643-11650, 1999.*
Zhou et al., Cell Mol Life Sci 63(19-20):2260-2290, 2006.*
Kozak, M., Gene 234:187-208, 1999.*
"Principles of Fermentation Technology", 1988, 85-86.
"Sakusankin Gluconoacetbacter Intermedius ni Okeru Quorum Sensing System no Kaiseiki", 2008, 237.
"Technology about Foam Formation: Use, Produce and Eliminate", 2004, 112-115.

* cited by examiner

*Primary Examiner* — Delia Ramirez
(74) *Attorney, Agent, or Firm* — Chainey P. Singleton; Edwin S. Flores; Chalker Flores, LLP

(57) ABSTRACT

The object of the present invention is to provide a method for suppressing foam formation by identifying a gene involved in foam formation during culture of an acetic acid bacterium and reducing or deleting the function of a protein encoded by the gene, a method for more efficiently producing vinegar that contains a high concentration of acetic acid by using an acetic acid bacterium in which foam formation has been suppressed by the above method, and vinegar produced by the above production method. An acetic acid bacterium with suppressed foam formation was obtained by isolating a gene encoding a protein involved in foam formation during culture of an acetic acid bacterium, then by altering the gene by a modification to reduce or delete the function of a protein involved in foam formation. Further provided is a method for efficiently producing vinegar with higher concentration of acetic acid with the use of the acetic acid bacterium.

3 Claims, 2 Drawing Sheets

1. Wild-type strain
2. orf3-disrupted strain
3. orf3-complementary strain

Wild-type strain orf3 disrupted strain 8h   12h   14h   17h   20h   24h   48h

Fig. 3

ATGCGGCCTT TTGCAAACGG AGAACTCGCT CTCCATCGCA GAAATAATCA TCAATATGGA

AACAGAAAAA TAAAACACAA GAGGACCAGA ACTTTGTTCT ACCGCGAAGG AGATATAGAA

TACCTAGCCC AAAAACTATT CTCTCAGCAC TATCCCTTTC GAAAGTGGGA CGACCGACCC

AATTCTATAT CGGGAGGCCC TACGCAAGAA GAAAAAGATA AATTCAAGGA TATCGCACGT

CAGCAATTAT CAGGCTGGCA CCCGGTA

Fig. 4

MetArgProPheAlaAsnGlyGluLeuAla LeuHisArgArgAsnAsnHisGlnTyrGly

AsnArgLysIleLysHisLysArgThrArg ThrLeuPheTyrArgGluGlyAspIleGlu

TyrLeuAlaGlnLysLeuPheSerGlnHis TyrProPheArgLysTrpAspAspArgPro

AsnSerIleSerGlyGlyProThrGlnGlu GluLysAspLysPheLysAspIleAlaArg

GlnGlnLeuSerGlyTrpHisProVal

Fig. 5

5'-CCGGAATTCGGATATGTCGCTCCCATTC-3'

Fig. 6

5'-GCGGGTACCCTGCGATGGAGAGCGAGTTCTC-3'

Fig. 7

5'-GGCAAGCTTGCAATTATCAGGCTGGCACC-3'

Fig. 8

5'-GCCAAGCTTACCAGGTGCGTGAGGGCATG-3'

Fig. 9

5'-CCGCCCGGGAAGCTTCACGCTGCCGCAAG-3'

Fig. 10

5'-GAGCCCGGGGTGGGCGAAGA-3'

GENE ASSOCIATED WITH FOAM FORMATION IN ACETIC ACID BACTERIUM, ACETIC ACID BACTERIUM MODIFIED TO REDUCE FOAM FORMATION, AND A METHOD FOR PRODUCING VINEGAR BY CULTURING AN ACETIC ACID BACTERIUM MODIFIED TO REDUCE FOAM FORMATION

CROSS-REFERENCE TO RELATED APPLICATIONS

This application is a 35 U.S.C. §371 national filing in the United States and claims priority to Japanese Patent Application Serial No. 2007-073498, filed Mar. 20, 2007, and PCT Application Serial No. PCT/JP2008/000571, filed Mar. 13, 2008, the entire contents of which are incorporated herein by reference.

TECHNICAL FIELD

The present invention relates to a gene involved in foam formation during microorganism culture, an acetic acid bacterium capable of reducing foam formation during culture and generating a larger amount of acetic acid by reducing or deleting the function of a protein encoded by the gene involved in foam formation, a method for producing vinegar using the acetic acid bacterium, and vinegar produced by the production method.

BACKGROUND ART

Foam formation during microorganism culture is a major concern in food industry and chemical industry where microorganisms are utilized. In many cases, foam is generated when microorganisms are cultured, especially when cultured under aeration and agitation. A foam layer is formed at the upper part of the culture tank and raises problems such as reduction of the working volume in the culture tank, or loss of the culture broth, compositional change of the broth and leakage of the microorganisms due to the outflow of the foam from the upper part of the tank. As such, foam formation causes problems including decrease in the production efficiency and deterioration in quality, and environmental pollution. For this reason, it has been a critical object to suppress foam formation in order to efficiently culture microorganisms for obtaining products. Decrease in the production efficiency due to foam formation has similarly been an object as well in the vinegar production using an acetic acid bacterium.

Therefore, physical and chemical methods have been developed as a defoaming method (see for example, Non-patent documents 1 and 2). As a physical method, there has been known for example, a mechanical method in which a shear force is applied to foam by such as an agitating blade to destroy the foam, a thermal method in which a liquid viscosity is decreased by heating to destabilize the foam, and an electric method in which foam is broken by such as energization, sparking and electric current. All of these methods, however, raise cost for introducing and using the equipments. In addition, defoaming effects brought by these methods have been insufficient.

As a chemical method, a method in which an antifoaming agent is added is exemplified. Compounds such as alcohols, esters, fatty acids and silicon oils are used as a antifoaming agent. However, while a defoaming method using a antifoaming agent is simple, there have been problems caused by some antifoaming agents such as decrease in the oxygen transfer rate which is important for microorganism growth and the material production, inhibition of the microorganism growth, and adverse influence on the isolation and purification steps.

Although the foam formation mechanism during microorganism culture remains largely unknown, some genes and proteins involved in foam formation in eukaryotes have been found. One of those genes is the awa1 gene which is involved in foam formation and found in the yeast (see for example, Non-patent document 3). This gene encodes the glycosylphosphatidylinositol anchor protein which is a protein specific to eukaryotes. This protein is involved in the cell surface hydrophobicity, and foaming ability is suppressed when the gene is disrupted. Further, a protein called hydrophobin which is either hydrophobic or amphipathic was found in fungi, mushrooms, etc. It has been found that the foaming ability is suppressed by disrupting a gene encoding the hydrophobin (see for example, Patent document 1). In prokaryotes, however, it is the current situation that knowledge of genes or proteins involved in foam formation during culture has scarcely been obtained, despite that breeding of bacterial strains with less foam formation had been desired as a novel defoaming means replacing physical or chemical methods.

On the other hand, the presence of an intercellular signal communication system in which transcription of specific genes is controlled depending on the cell density has been recently elucidated in many bacteria. This system is called quorum-sensing system (a control system sensing a cell density) and is involved in the expression control for various functions such as bioluminescence, exoenzyme production, toxic virulence, biofilm formation, and antibiotic production.

Two kinds of proteins are involved in the quorum-sensing system which has been found in many Gram negative bacteria such as *Vibrio fischeri* (see for example, Non-Patent document 4). The proteins are an acyl homoserine lactone synthase that synthesizes acyl homoserine lactone which is an intracellular signal molecule, and an acyl homoserine lactone receptor-type transcription factor that is a receptor of acyl homoserine lactone and that also functions as a transcription factor. Acyl homoserine lactone produced by an acyl homoserine lactone synthase in a bacterial cell diffuses inside and outside the bacterial cell. As the concentration of acyl homoserine lactone is increased, it forms a complex with the acyl homoserine lactone receptor-type transcription factor in a bacterial cell to control the gene transcription.

The present inventor has already obtained two kinds of genes involved in the quorum-sensing system in an acetic acid bacterium, namely, a gene encoding the acyl homoserine lactone synthase and a gene encoding the acyl homoserine lactone receptor-type transcription factor. In addition, the present inventor has demonstrated that the quorum-sensing system in an acetic acid bacterium is involved in the acetic acid production ability. However, the correlation between the quorum-sensing system and foam formation during microorganism culture has been totally unknown.

Non-Patent Document 1: Principles of Fermentation Technology, Japan Scientific Societies Press, p. 85-86, 1988

Non-Patent Document 2: Technology about foam formation: Use, produce and eliminate, Kogyo Chosakai Publishing, Inc., p. 112-115, 2004

Non-Patent Document 3: Journal of bioscience and bioengineering, Vol. 97, No. 1, pp. 14-18, 2004

Non-Patent Document 4: Bioscience and Industry, Vol. 60, No. 4, pp. 219-224, 2002

Patent Document 1: Published Japanese translation of PCT international publication No. 2003-507056

DISCLOSURE OF THE INVENTION

Object to be Solved by the Invention

The objects of the present invention are to provide a method for suppressing foam formation by identifying a gene involved in foam formation during culture of an acetic acid bacterium and reducing or deleting the function of a protein encoded by the gene, a method for more efficiently producing vinegar containing a high concentration of acetic acid by using the acetic acid bacterium with suppressed foam formation by the method, and vinegar produced by said production method.

Means to Solve the Object

The present inventor focused on genes involved in the quorum-sensing system. The present inventor thus conducted various experiments in order to obtain a gene involved in the quorum-sensing system of an acetic acid bacterium by the methods including a genomic southern blotting based on conventionally known genes involved in the quorum-sensing system or PCR method using degenerate primers prepared based on the sequence information of the known genes, but without success. (The cause for the failure turned out to be the low homology at last upon performing the sequence analysis of genes involved in a quorum-sensing system of an acetic acid bacterium after the cloning.) Therefore, the present inventor started to try a cloning method for genes involved in the quorum-sensing system using a reporter strain as an indicator. Several thousand colonies of a chromosomal DNA library prepared by shotgun cloning were tested using several reporter strains. However, not all of the reporter strains brought success, and cloning of genes involved in a quorum-sensing system did not succeed at first. In an assay in which *Agrobacterium tumefaciens* NTL4 (pZLR4) was selected as a reporter strain after having used the above several reporter strains, cloning of genes involved in the quorum-sensing system of an acetic acid bacterium was at last succeeded after testing several thousand colonies of the chromosomal DNA library prepared by shotgun cloning.

In this way, genes encoding two kinds of proteins that are involved in the quorum-sensing system in an acetic acid bacterium, that is, genes encoding the acyl homoserine lactone synthase and the acyl homoserine lactone receptor-type transcription factor were found in an acetic acid bacterium for the first time (Japanese Patent Application No. 2007-43635). On the other hand, because foam formation occurs at the later stage of culture, the present inventor happened to focus on the correlation between the quorum-sensing system, which is a transcriptional regulation system depending on the bacterial cell density, and foam formation. Then, in order to investigate influence of the quorum-sensing system on the foaming ability, the present inventor analyzed the phenotypes of strains in which both genes were disrupted respectively, and found that the foaming ability was suppressed in both disruptant strains. As a result of further analysis for investigating the causal genes for foam formation, the present inventor found a novel gene with unknown function which forms an operon with the gene encoding the acyl homoserine lactone synthase, to the downstream of said gene, and found that the gene encodes a protein involved in foam formation.

It was subsequently confirmed that foam formation during culture is significantly suppressed by reducing or deleting the function of a protein involved in foam formation by modifying the above-mentioned gene, and vinegar containing a high concentration of acetic acid can be produced more efficiently. The present invention has thus been completed.

The present invention relates to the following.

(1) A protein shown by following (A), (B) or (C):
(A) a protein consisting of the amino acid sequence shown by SEQ ID NO: 2 in the sequence listing;
(B) a protein which consists of an amino acid sequence wherein one or a few amino acids are substituted, deleted, inserted or added in the amino acid sequence shown by SEQ ID NO: 2 in the sequence listing, and which is involved in foam formation in a culture broth of an acetic acid bacterium;
(C) a protein which consists of an amino acid sequence having at least 85% or more identity to the amino acid sequence shown by SEQ ID NO: 2 in the sequence listing, and which is involved in foam formation in a culture broth of an acetic acid bacterium.

(2) A DNA encoding a protein shown by following (A), (B) or (C):
(A) a protein consisting of the amino acid sequence shown by SEQ ID NO: 2 in the sequence listing;
(B) a protein which consists of an amino acid sequence wherein one or a few amino acids are substituted, deleted, inserted or added in the amino acid sequence shown by SEQ ID NO: 2 in the sequence listing, and which is involved in foam formation;
(C) a protein which consists of an amino acid sequence having at least 85% or more identity to the amino acid sequence shown by SEQ ID NO: 2 in the sequence listing, and which is involved in foam formation in a culture broth of an acetic acid bacterium.

(3) A DNA shown by following (A), (B), (C) or (D)
(A) a DNA consisting of the nucleotide sequence shown by SEQ ID NO: 1 in the sequence listing;
(B) a DNA which hybridizes under stringent conditions to a DNA consisting of a sequence complementary to the nucleotide sequence shown by SEQ ID NO: 1 in the sequence listing, and which encodes a protein involved in foam formation;
(C) a DNA which hybridizes under stringent conditions to a DNA consisting of a nucleotide sequence produced from a part of the nucleotide sequence shown by SEQ ID NO: 1 in the sequence listing and having a function as a primer or a probe, and which encodes a protein involved in foam formation in a culture broth of an acetic acid bacterium;
(D) a DNA which consists of a nucleotide sequence wherein one or a few nucleotides are substituted, deleted, inserted or added in the nucleotide sequence shown by SEQ ID NO: 1 in the sequence listing, and which encodes a protein involved in foam formation in a culture broth of an acetic acid bacterium.

(4) A method for producing an acetic acid bacterium with suppressed foaming ability, wherein the function of a protein which is encoded by a gene involved in foam formation of an acetic acid bacterium is reduced or deleted.

(5) The method for producing an acetic acid bacterium with suppressed foaming ability according to (4), wherein the gene involved in foam formation of an acetic acid bacterium is a gene involved in the quorum-sensing system in an acetic acid bacterium.

(6) The method for producing an acetic acid bacterium with suppressed foaming ability according to (5), wherein the gene involved in foam formation of an acetic acid bacterium is a gene consisting of the DNA according to (2) or (3).

(7) An acetic acid bacterium with suppressed foaming ability which is obtained by the method according to any one of (4) to (6).

(8) The acetic acid bacterium with suppressed foaming ability according to (7), wherein the acetic acid bacterium is *Gluconacetobacter intermedius* NCI1051Δorf3 (FERM BP-10792).

(9) A method for producing vinegar comprising culturing the acetic acid bacterium according to (7) or (8) in an alcohol-containing medium, and generating and accumulating acetic acid in the medium.

Effect of the Invention

According to the present invention, a gene involved in foam formation of an acetic acid bacterium and the protein thereof are provided. Further provided is a method for significantly suppressing foam formation during culture by reducing or deleting the function of a protein encoded by the gene. Still further, a method is provided wherein vinegar containing a high concentration of acetic acid is more efficiently produced by significantly suppressing foam formation during culture, and vinegar containing a high concentration of acetic acid produced by said production method is also provided.

BRIEF EXPLANATION OF THE DRAWINGS

FIG. 3 shows the nucleotide sequence of a DNA fragment comprising orf3 (SEQ ID NO: 1).

FIG. 4 shows the amino acid sequence of orf3 (SEQ ID NO: 2).

FIG. 5 shows the nucleotide sequence of primer 1 (SEQ ID NO: 3).

FIG. 6 shows the nucleotide sequence of primer 2 (SEQ ID NO: 4).

FIG. 7 shows the nucleotide sequence of primer 3 (SEQ ID NO: 5).

FIG. 8 shows the nucleotide sequence of primer 4 (SEQ ID NO: 6).

FIG. 9 shows the nucleotide sequence of primer 5 (SEQ ID NO: 7).

FIG. 10 shows the nucleotide sequence of primer 6 (SEQ ID NO: 8).

BEST MODE OF CARRYING OUT THE INVENTION

Figure 1:
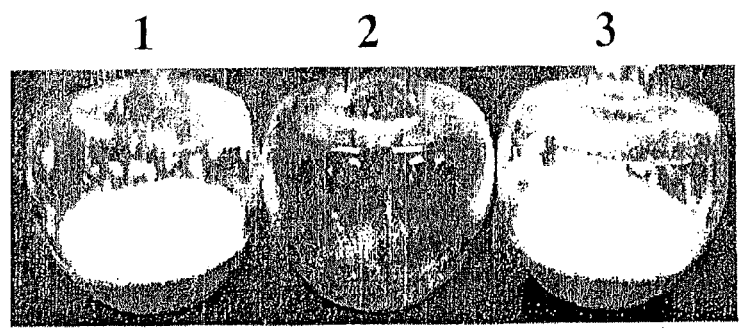
FIG. 1 shows the aspect of foam formation when the wild-type strain and the orf3-disrupted strain were cultured.

The present invention is explained in detail in the following.

A protein of the present invention is a protein involved in foam formation of an acetic acid bacterium. Specifically, it relates to a protein consisting of the amino acid sequence shown by SEQ ID NO: 2 (FIG. 4) in the sequence listing; a protein which consists of an amino acid sequence wherein one or a few amino acids are substituted, deleted, inserted or added in the amino acid sequence shown by SEQ ID NO: 2 (FIG. 4) in the sequence listing, and which is involved in foam formation; and a protein which consists of an amino acid sequence having at least 85% or more identity to the amino acid sequence shown by SEQ ID NO: 2 (FIG. 4) in the sequence listing, and which is involved in foam formation. "A protein which is involved in foam formation" in the present invention refers to a protein wherein foam formation during culture of an acetic acid bacterium is suppressed by reducing or deleting the function of the protein.

The method of obtaining and preparing a protein of the present invention is not particularly limited and the protein may be any of an isolated naturally-occurring protein, chemically synthesized protein, or a recombinant protein prepared by a gene recombination technique. When obtaining a naturally-occurring protein of the present invention, the protein can be obtained from the cells expressing it by appropriately combining isolation and purification methods for proteins.

When preparing a protein of the present invention by chemical synthesis, the protein of the present invention can be synthesized according to a chemical synthesis method such as Fmoc method (fluorenylmethyloxycarbonyl method), tBOC method (t-butyloxycarbonyl method) or the like. A protein of the present invention can also be synthesized by utilizing various commercially-available peptide synthesizers based on the amino acid sequence information.

Further, when preparing a protein of the present invention by a gene recombination technique, a protein of the present invention can be prepared by introducing a DNA encoding the protein into a suitable expression system. Among these methods, it is preferred to prepare a protein of the present invention by a gene recombination technique which enables the preparation with a relatively easy operation at a large quantity.

When preparing a protein of the present invention by a gene recombination technique, known methods including anion- or cation-exchange chromatography; phosphocellulose chromatography; hydrophobic interaction chromatography; affinity chromatography; hydroxyapatite chromatography; and lectin chromatography may be employed after performing ammonium sulfate or ethanol precipitation and acid extraction to recover and purify the protein from the cell culture, where a high-speed liquid chromatography is preferably employed.

Particularly, the purified products of these proteins can be obtained with affinity chromatography using a column to which an antibody such as a monoclonal antibody against a protein of the present invention is bound, or a column to which a substance having affinity to the peptide tag is bound when a usual peptide tag has been added to a protein of the present invention.

Further, a protein consisting of an amino acid sequence wherein one or a few amino acids are substituted, deleted, inserted or added in the amino acid sequence shown by SEQ ID NO: 2 (FIG. 4) in the sequence listing, or a protein consisting of an amino acid sequence having at least 85% or more identity to the amino acid sequence shown by SEQ ID NO: 2 (FIG. 4) in the sequence listing can be appropriately prepared or obtained by a skilled person in the art based on the nucleotide sequence information shown by SEQ ID NO: 1 (FIG. 3) in the sequence listing which is an example of the nucleotide sequences encoding the amino acid sequence shown by SEQ ID NO: 2 (FIG. 4).

For example, a homologue of the DNA can be isolated from acetic acid bacteria belonging to the genus *Acetobacter* or the genus *Gluconacetobacter*, or from other acetic acid bacteria by carrying out a screening under appropriate conditions by a polymerase chain reaction (PCR reaction) that uses as a primer an oligonucleotide synthesized based on the nucleotide sequence shown by SEQ ID NO: 1 (FIG. 3) in the sequence listing, or by a hybridization using as a probe an oligonucleotide synthesized based on the above nucleotide sequence. The full-length DNA of the homologous DNA is cloned, integrated into an expression vector and expressed in an appropriate host, and the protein encoded by the homologous DNA can be prepared.

An oligonucleotide can be synthesized according to a conventional method using, for example, various commercially-available DNA synthesizers. Further, a PCR reaction can be performed according to a conventional method using a thermal cycler, Gene Amp PCR System 2400 manufactured by Applied Biosystems, with the use of TaqDNA polymerase (Takara Bio Inc.) or KOD-Plus (Toyobo Co., Ltd.).

It is also possible to bind the above protein of the present invention with a marker protein and/or a peptide tag to provide a fusion protein. The marker protein is not particularly limited as long as it is a conventionally known marker protein. Specific examples of the marker protein include enzymes such as alkaline phosphatase and HRP, the Fc region of an antibody, and a fluorescent material such as GFP. Further, specific examples of the peptide tag include conventionally known peptide tags including epitope tags such as HA, FLAG, Myc; and affinity tags such as GST, maltose-binding protein, biotinated peptide, and oligohistidine. The fusion protein can be produced by a common method, and is useful for a purification of a protein of the present invention, a detection of a protein of the present invention and a quantitative determination of an antibody against a protein of the present invention by utilizing affinity between Ni-NTA and His tag. The fusion protein is also useful as a laboratory reagent in the field to which the present invention pertains.

Further, examples of a DNA of the present invention include: a DNA encoding a protein consisting of the amino acid sequence shown by SEQ ID NO: 2 (FIG. 4) in the sequence listing; a DNA encoding a protein which consists of an amino acid sequence wherein one or a few amino acids are substituted, deleted, inserted or added in the amino acid sequence shown by SEQ ID NO: 2 (FIG. 4) in the sequence listing, and which is involved in foam formation; a DNA encoding a protein which consists of an amino acid sequence having at least 85% or more identity to the amino acid sequence shown by SEQ ID NO: 2 (FIG. 4) in the sequence listing, and which is involved in foam formation; a DNA which hybridizes under stringent conditions to a DNA consisting of the nucleotide sequence shown by SEQ ID NO: 1 (FIG. 3) in the sequence listing or a DNA consisting of a sequence complementary to the nucleotide sequence shown by SEQ ID NO: 1 (FIG. 3) in the sequence listing, and which encodes a protein involved in foam formation; a DNA which hybridizes under stringent conditions to a DNA consisting of a nucleotide sequence prepared from a part of the nucleotide sequence shown by SEQ ID NO: 1 (FIG. 3) in the sequence listing and having a function as a primer or a probe, and which encodes a protein involved in foam formation; and a DNA which consists of a nucleotide sequence wherein one or a few nucleotides are substituted, deleted, inserted or added in the nucleotide sequence shown by SEQ ID NO: 1 (FIG. 3) in the sequence listing, and which encodes a protein involved in foam formation.

As above, a DNA encoding a protein involved in foam formation of the present invention may be a DNA that encodes a protein having deletion, substitution, insertion or addition of one or a few amino acids at a single site or plural sites, as long as the function of the encoded protein is not impaired.

A DNA encoding a protein that is substantially the same as a protein having the function of a protein involved in foam formation can be obtained by alteration of a nucleotide sequence, such modification being a substitution, deletion, insertion, addition, or inversion of an amino acid at a particular site by means of, for example, site-directed mutagenesis. Further, an altered DNA such as the above can also be obtained by a conventionally known mutagenic treatment. Still further, it is possible to obtain a DNA that encodes substantially the same protein from acetic acid bacteria in general, or from species, strains, mutants, or variants of the genus *Acetobacter* or the genus *Gluconacetobacter*, in particular, because it is generally known that an amino acid sequence of a protein and a nucleotide sequence encoding the same are slightly different among the species, strains, mutants or variants.

The above "amino acid sequence wherein one or a few amino acids are substituted, deleted, inserted or added" means, for example, an amino acid sequence wherein any number of amino acids, for example, 1 to 20, preferably 1 to 15, more preferably 1 to 10, and still more preferably 1 to 5' amino acids, are substituted, deleted, inserted or added.

Further, the above "nucleotide sequence wherein one or a few nucleotides are substituted, deleted, inserted or added" means, for example, a nucleotide sequence wherein any number of nucleotides, for example, 1 to 20, preferably 1 to 15, more preferably 1 to 10, and still more preferably 1 to 5 nucleotides are substituted, deleted, inserted or added.

For example, these DNAs consisting of a nucleotide sequence comprising a substitution, deletion, insertion, or addition of one or a few nucleotides (mutated DNAs) can also be prepared by any method known to a skilled person in the art, such as chemical synthesis, genetic engineering technique, and mutagenesis, as stated above. Specifically, mutated DNAs can be obtained by introducing a mutation into the DNA consisting of the nucleotide sequence shown by SEQ ID NO: 1 in the sequence listing, using a method of allowing a mutagenic agent to contact with and act on the DNA; a method of irradiating the DNA with ultraviolet; a genetic engineering technique or the like. The site-directed mutagenesis, one of the genetic engineering techniques, is useful as it is a technique that allows an introduction of a specific mutation into a specific site, and can be performed according to the method described in Molecular Cloning: A laboratory Manual, 2nd Ed., Cold Spring Harbor Laboratory, Cold Spring Harbor, N.Y., 1989, or in Current Protocols in Molecular Biology, Supplement 1-38, John Wiley & Sons (1987-1997), or the like. An expression of this mutated DNA using an appropriate expression system provides a protein consisting of an amino acid sequence comprising a substitution, deletion, insertion or addition of one or a few amino acids.

The above "amino acid sequence having at least 85% or more identity to the amino acid sequence shown by SEQ ID NO: 2 (FIG. 4) in the sequence listing" is not particularly limited as long as the identity to the amino acid sequence shown by SEQ ID NO: 2 (FIG. 4) in the sequence listing is 85% or more. This means that the identity is, for example, 85% or more, preferably 90% or more, more preferably 95% or more, and particularly preferably 98% or more.

The above "under stringent conditions" refers to a condition under which a so-called specific hybrid is formed while a non-specific hybrid is not formed. Specific examples include a condition under which DNAs sharing 50% or more, preferably 70% or more identity hybridize each other, while DNAs with the lower identity do not hybridize; or a hybridization condition at a salt concentration corresponding to 1×SSC (1-fold-concentration SSC solution comprises 150 mM NaCl and 15 mM sodium citrate) and 0.1% SDS, or 0.1×SSC and 0.1% SDS at 65° C., which are washing conditions for a usual southern hybridization.

Further, the above "DNA that hybridizes under stringent conditions" means a DNA that can be obtained by using a method such as a colony hybridization, plaque hybridization or southern-blot hybridization using nucleic acids such as DNA or RNA as a probe. Specifically exemplified is a DNA that can be identified by conducting a hybridization at 65° C.

in the presence of 0.7 to 1.0 M NaCl using a filter on which a colony- or plaque-derived DNA or a fragment thereof is immobilized, and washing the filter under the condition of 65° C. with about 0.1 to 2-fold-concentration SSC solution.

Hybridization can be performed according to the method described in Molecular Cloning: A laboratory Manual, 2nd Ed., Cold Spring Harbor Laboratory, Cold Spring Harbor, N.Y., 1989 or the like. Examples of a DNA that can hybridize under stringent conditions include a DNA having an identity above a certain level to a nucleotide sequence of a DNA used as a probe. A DNA having an identity of, for example, 60% or more, preferably 70% or more, more preferably 80% or more, still more preferably 90% or more, particularly preferably 95% or more, and most preferably 98% or more, can be exemplified advantageously.

A method of obtaining or preparing a DNA of the present invention is not particularly limited. The DNA of interest can be isolated by preparing an appropriate probe or primer based on the nucleotide sequence information shown by SEQ ID NO: 1 (FIG. 3) in the sequence listing or the amino acid sequence information shown by SEQ ID NO: 2 (FIG. 4) in the sequence listing disclosed herein, and using the probe or primer for screening a cDNA library where the DNA is expected to exist, or the DNA can be prepared by chemical synthesis according to a common method.

A genomic DNA of the present invention can be obtained, for example, by preparing a cDNA library according to a common method from acetic acid bacteria belonging to the genus *Acetobacter* or the genus *Gluconacetobacter*, and then selecting from this library a desired clone using an appropriate probe which is specific to the genomic DNA of the present invention. Further, isolation of total RNA, isolation and purification of mRNAs, acquisition and cloning of cDNAs and the like from these acetic acid bacteria can all be performed according to a common method. Examples of the method of screening a genomic DNA of the present invention from a cDNA library include the methods commonly used by a skilled person in the art such as a method described in Molecular Cloning, 2nd ed.

Since the nucleotide sequence of a DNA of the present invention has already been elucidated, the DNA can be obtained by a PCR reaction using the oligonucleotide synthesized based on the nucleotide sequence as a primer or by hybridization using the oligonucleotide synthesized based on the nucleotide sequence as a probe, with the use of, for example, the genomic DNA of the acetic acid bacterium, *Gluconacetobacter intermedius* NCI 1051, as a template. The chromosomal DNA can be obtained by a common method disclosed (e.g., Japanese Laid-Open Patent Application No. 60-9489).

An oligonucleotide can be synthesized according to a common method using, for example, various commercially-available DNA synthesizers. Further, a PCR reaction can be performed according to a common method using a thermal cycler, Gene Amp PCR System 2400 manufactured by Applied Biosystems, with the use of TaqDNA polymerase (Takara Bio Inc.), KOD-Plus (Toyobo Co., Ltd.), etc.

A DNA of the present invention can be obtained by alteration of a nucleotide sequence, such alteration being a substitution, deletion, insertion or addition of amino acids at a specific site by means of, for example, site-directed mutagenesis. Further, an altered DNA such as the above can also be obtained by a conventionally known mutagenic treatment.

Still further, it is possible to obtain a DNA that encodes substantially the same protein from general acetic acid bacteria, in particular, from species, strains, mutants or variants of the genus *Acetobacter* or the genus *Gluconacetobacter*, because it is generally known that an amino acid sequence of a protein and a nucleotide sequence encoding the same are slightly different among the species, strains, mutants or variants.

Specifically, by isolating a DNA which hybridizes under stringent conditions to a DNA comprising a nucleotide sequence described in the nucleotide sequence shown by SEQ ID NO: 1 (FIG. 3) in the sequence listing, and which encodes a protein involved in foam formation from acetic acid bacteria belonging to the genus *Acetobacter* or the genus *Gluconacetobacter*, or mutated acetic acid bacteria belonging to the genus *Acetobacter* or the genus *Gluconacetobacter*, or from spontaneous mutants or variants thereof, it is also possible to obtain a DNA encoding a protein that is substantially the same as the above protein.

A mutant gene or homologous gene of the present invention consisting of a DNA encoding a protein consisting of an amino acid sequence wherein one or a few amino acids are substituted, deleted, inserted or added in the amino acid sequence shown by SEQ ID NO: 2 (FIG. 4) in the sequence listing and involved in foam formation, or a DNA encoding a protein consisting of an amino acid sequence having at least 85% or more identity to the amino acid sequence shown by SEQ ID NO: 2 (FIG. 4) in the sequence listing and having a function as a protein involved in foam formation, etc., can be isolated from other acetic acid bacteria or the like by screening a homologue of the above DNA under appropriate conditions with the use of a DNA fragment comprising the nucleotide sequence shown by SEQ ID NO: 1 (FIG. 3) in the sequence listing or a part thereof. The variant gene or homologous gene can also be prepared by a production method of an altered DNA as described above.

By isolating a DNA which hybridizes under stringent conditions to a probe prepared from the nucleotide sequence shown by SEQ ID NO: 1 in the sequence listing or from a part thereof from acetic acid bacteria belonging to the genus *Acetobacter* or the genus *Gluconacetobacter*, or mutated acetic acid bacteria belonging to the genus *Acetobacter* or the genus *Gluconacetobacter*, or from spontaneous mutants or variants thereof, and which encodes a protein involved in foam formation, it is also possible to obtain a DNA encoding a protein that is substantially the same as the above protein.

An acetic acid bacterium of the present invention is not particularly limited and is exemplified by a bacterium belonging to such as the genus *Acetobacter* or the genus *Gluconacetobacter* that have alcohol oxidation ability. An acetic acid bacterium of the present invention, however, is characterized in that it has been altered so that the function of a protein encoded by the gene involved in foam formation has been reduced or deleted as described above. Examples of the acetic acid bacterium include the following.

Examples of the acetic acid bacterium belonging to the genus *Gluconacetobacter* include *Gluconacetobacter intermedius, Gluconacetobacter xylinus, Gluconacetobacter europaeus, Gluconacetobacter diazotrophicus* and *Gluconacetobacter entanii*, and more specifically include *Gluconacetobacter xylinus* IFO3288, *Gluconacetobacter europaeus* DSM6160, *Gluconacetobacter diazotrophicus* ATCC49037, *Acetobacter altoacetigenes* MH-24, and *Gluconacetobacter intermedius* NCI1051 (FERN BP-10767).

Further, examples of the acetic acid bacterium belonging to the genus *Acetobacter* include *Acetobacter aceti*, and more specifically include *Acetobacter aceti* No. 1023 and *Acetobacter aceti* IFO3283.

The method for producing an acetic acid bacterium with suppressed foaming ability by reducing or deleting the function of a protein encoded by the gene involved in foam formation of an acetic acid bacterium of the present invention (i.e., a gene encoding a protein involved in foam formation of an acetic acid bacterium) is exemplified by a method which comprises culturing an acetic acid bacterium under the physical conditions that inhibits the expression of the gene encoding a protein involved in foam formation of an acetic acid bacterium or the activity of a protein encoded by the gene.

It is also effective to reduce or delete the function by modifying a gene involved in foam formation of an acetic acid bacterium. It is also effective to induce a mutation in a region of the gene where it is involved in the expression of the gene so as to inhibit the expression thereof. As a method to modify a gene, a method in which mutation is induced to the gene by a physical treatment or by using a chemical mutagenic agent is effective. As these methods for inducing mutation, methods conventionally practiced for acetic acid bacteria are effective. Examples of such conventional method include a method for inducing mutation by subjecting an acetic acid bacterium to an ultraviolet irradiation or treating an acetic acid bacterium with N-methyl-N'-nitro-N-nitrosoguanidine (NTG) or with a mutagenic agent usually used for mutagenic treatment such as nitrous acid.

Since acetic acid bacteria are known as bacteria that tend to mutate spontaneously, an acetic acid bacterium with suppressed foaming ability can also be obtained by isolating from the nature an acetic acid bacterium having a gene in which expression or function of the above enzyme has been spontaneously mutated. Further, since these genes have already been obtained and the nucleotide sequences thereof have also been elucidated, it is also effective to subject these genes to recombination for introducing mutagenesis, then to introduce the mutated gene into the original acetic acid bacterium, and to reduce or delete the function of the gene of the original acetic acid bacterium by employing such as a homologous recombination. For example, a method is effective wherein the method comprises: transforming an acetic acid bacterium with a DNA comprising a gene that has been modified so as not to produce a normally functioning protein involved in foam formation by deleting a partial sequence of the gene or by inserting a drug-resistant gene into the gene; and disrupting a normal gene on the chromosome by a homologous recombination.

Further, when a gene involved in foam formation of the present invention is controlled by the quorum-sensing system, it is also possible to reduce or delete the function of a protein encoded by the gene involved in foam formation by reducing or deleting the function of the system. For example, an acetic acid bacterium with suppressed foaming ability wherein a function of the acyl homoserine lactone synthase and/or acyl homoserine lactone receptor-type transcription factor is reduced or deleted can be prepared by disrupting the gene of acyl homoserine lactone synthase and/or the gene of acyl homoserine lactone receptor-type transcription factor.

Transformation of an acetic acid bacterium may be conducted by such as a calcium chloride method (see for example, Agric. Biol. Chem., Vol. 49, p. 2091; 1985), and an electroporation method (see for example, Biosci. Biotech. Biochem., Vol. 58, p. 974, 1994).

As above, foam formation during culture can be suppressed in an acetic acid bacterium belonging to the genus *Acetobacter* or the genus *Gluconacetobacter* having the alcohol oxidation ability by altering a protein involved in foam formation by reducing or deleting the function as stated above so that the protein does not function normally.

Examples of the acetic acid bacterium with suppressed foaming ability of the present invention specifically include *Gluconacetobacter intermedius* NCI 1051Δorf3 (FERN BP-10792), *Gluconacetobacter intermedius* NCI 1051Δorf1 (FERN BP-10768) in which a gene encoding the acyl homoserine lactone synthase is disrupted, and *Gluconacetobacter intermedius* NCI 1051Δorf2 (FERN BP-10769) in which a gene encoding the acyl homoserine lactone receptor-type transcription factor is disrupted. The NCI 1051Δorf3 is preferably exemplified among these.

A conventionally known method is employed for the method of producing vinegar of the present invention except that the function of a protein involved in foam formation of an acetic acid bacterium is reduced or deleted so that the protein does not function normally, and culturing the acetic acid bacterium in an alcohol-containing medium to generate and accumulate acetic acid in the medium. Namely, an acetic acid bacterium may be cultured basically under the conditions where acetic acid fermentation can be performed. Specifically, the culture of an acetic acid bacterium may be conducted similarly to that in a production method of vinegar that employs a conventional fermentation method for acetic acid.

As for an alcohol-containing medium, any medium suffices as long as it is a medium used for acetic acid fermentation. Those alcohol-containing media may be used that contain a carbon source, nitrogen source, inorganic substance, etc. other than an alcoholic component such as ethanol, and contain an appropriate amount of nutrient source required for growth of a bacterial strain in use, if necessary. A medium may be either a synthetic medium or a natural medium. Examples of the carbon source include various carbohydrates including glucose and sucrose, and various organic acids. As a nitrogen source, a natural nitrogen source such as peptone, degradation product of microbial cells or the like can be used.

Further, the culture is performed under an aerobic condition such as in a static culture, shaking culture, aeration-agitation culture and the like. The culture is performed at the temperature of 25 to 35° C., and usually at 30° C. The pH of medium is generally within the range of 2.5 to 7, preferably within the range of 2.7 to 6.5, and the pH can also be adjusted with various acids, various bases, buffers or the like. Generally, a 1- to 21-day culture can accumulate a high concentration of acetic acid in the medium. A high acidity vinegar with suppressed foam formation during culture can be produced more efficiently by the above method for producing vinegar of the present invention.

The present invention is specifically explained in the following with reference to the examples. The technical scope of the present invention, however, will not be limited to these exemplifications.

EXAMPLE 1

Gene Involved in Foam Formation

Since foam formation in the culture broth occurs at a later stage of the culture, it was thought that foam formation might be under the control of the quorum-sensing system which is a transcriptional regulation system depending on bacterial cell density. Therefore, the foaming ability of *Gluconacetobacter intermedius* NCI 1051Δorf1 (hereinafter may be referred to as orf1-disrupted strain) and *Gluconacetobacter intermedius* NCI-1051Δorf2 (hereinafter may be referred to as orf2-disrupted strain) were respectively compared to the foaming ability of *Gluconacetobacter intermedius* NCI 1051 (herein after may be referred to as wild-type strain). Here, the *Gluconacetobacter intermedius* NCI 1051Δorf1 in which a gene encoding the acyl homoserine lactone synthase is disrupted is a strain derived from *Gluconacetobacter intermedius* NCI 1051 that was deposited under the Budapest Treaty on Jan. 31, 2007 with the International Patent Organism Depositary at the National Institute of Advanced Industrial Science and Technology (Central 6, 1-1 Higashi 1-Chome, Tsukuba-shi, Ibaraki-ken, Japan) under the Accession Number FERM BP-10767, and the NCI-1051Δorf1 itself was also deposited under the Budapest Treaty on Jan. 31, 2007 with the same depositary under the Accession Number FERM BP-10768; and the *Gluconacetobacter intermedius* NCI-1051Δorf2 in which a gene encoding the acyl homoserine lactone receptor-type transcription factor is disrupted was deposited under the Budapest Treaty on Jan. 31, 2007 with the same depositary under the Accession Number FERN BP-10769.

Specifically, a shaking culture was carried out at 30° C. and 120 rpm in a 100 ml medium containing 2% ethanol, 3% glucose, 0.5% yeast extract, 0.3% polypeptone, 100 μg/ml ampicillin, and 1% Celluclast 1.5 L (Novozymes) by using a Sakaguchi flask of 500 ml volume. As a result, it was demonstrated that foam formation was significantly suppressed in the orf1-disrupted strain and the orf2-disrupted strain as compared to the wild-type strain. This result suggested that foam formation during culture of an acetic acid bacterium is controlled by the quorum-sensing system.

In order to confirm the above result, it was attempted to prepare the complementary strains of orf1 and orf2. Consequently, it was demonstrated that orf3, which is present as an operon to the downstream of orf1, is necessary for complementing the orf1-disrupted strain. The nucleotide sequence of a DNA containing orf3 was determined to be FIG. 3 and SEQ ID NO: 1, and orf3 was confirmed to correspond to nucleotide numbers 1-267 in the SEQ ID NO: 1.

The above results suggested that orf3 is a gene involved in foam formation.

Consequently, a homology search was conducted for the orf3 gene which consists of the nucleotide sequence shown in FIG. 3 and by nucleotide numbers 1-267 in SEQ ID NO: 1 in the sequence listing. The result of the search demonstrated that there is no other sequences sharing a significant homology to the orf3 gene and that the gene is a novel gene. A complementary strain was also prepared for orf2, and it Was confirmed that the phenotype was restored.

EXAMPLE 2

Strain in which the Gene Involved in Foam Formation is Disrupted

In Example 1, orf3 was suggested to be a gene involved in foam formation. Therefore, a orf3-disrupted strain was prepared to examine the involvement of orf3 in foam formation. Namely, using primer 1 (see FIG. 5 and SEQ ID NO: 3 in the sequence listing) and primer 2 (see FIG. 6 and SEQ ID NO: 4 in the sequence listing) which were synthesized based on the nucleotide sequence of orf3, an upstream sequence and 5'-side sequence of orf3 was amplified by PCR method with the chromosomal DNA of *Gluconacetobacter intermedius* NCI 1051 as a template, and the amplified product was treated with the restriction enzymes EcoRI and KpnI (TAKARA BIO INC.) to prepare a DNA fragment (DNA fragment 1).

Similarly, using primer 3 (see FIG. 7 and SEQ ID NO: 5 in the sequence listing) and primer 4 (see FIG. 8 and SEQ ID NO: 6 in the sequence listing) which were synthesized, a 3'-side sequence and downstream sequence of orf3 was amplified by PCR method with the chromosomal DNA of *Gluconacetobacter intermedius* NCI 1051 as a template, and the amplified product was treated with the restriction enzyme Hind III (TAKARA BIO INC.) to prepare a DNA fragment (DNA fragment 2).

Further, a DNA fragment including a Kanamycin-resistant gene was amplified by FOR method using primer 5 (see FIG. 9 and SEQ ID NO: 7 in the sequence listing) and primer 6 (see FIG. 10 and SEQ ID NO: 8 in the sequence listing) with transposon Tn5 of *Escherichia coli* as a template, and the amplified product was treated with the restriction enzyme Sma I (TAKARA BIO INC.) to prepare a DNA fragment (DNA fragment 3).

The chromosomal DNA was extracted by using GenomicPrep Cells and Tissue DNA Isolation Kit (Amersham Bioscience). A PCR reaction was conducted for 30 cycles with each cycle consisting of denaturation at 94° C. for 30 seconds, annealing at 55° C. for 30 seconds, and elongation at 72° C. for 1 minute, by using Pyrobest DNA Polymerase (TAKARA BIO INC.). Subsequently, the DNA fragment 3 was ligated to the Sma I site in pUC18. Thus prepared DNA was transformed into *Escherichia coli* JM109 strain by electroporation method (see Biosci. Biotech. Biochem., Vol. 58, p. 974, 1994).

Transformants were selected on a LB agar medium supplemented with 100 μg/ml ampicillin. A plasmid DNA was prepared, according to a common method, from the ampicillin-resistant transformant grown on the above selection medium. The DNA fragment 1 was linked to EcoRI-kpnI site and the DNA fragment 2 was similarly linked to Hind III site of thus obtained plasmid DNA to transform *Escherichia coli* strain, and the plasmid pUCΔorf3 for disrupting orf3 was prepared.

Thus obtained plasmid pUCΔorf3 for disrupting orf3 was used to transform *Gluconacetobacter intermedius* NCI 1051 (hereinafter may be referred to as wild-type strain) by electroporation method (Proc. Natl. Acad. Sci. U.S.A., Vol. 87, pp. 8130-8134, 1990).

Transformants were selected on a YPG medium (3% glucose, 0.5% yeast extract and 0.3% polypeptone) supplemented with 100 μg/ml kanamycin. A chromosomal DNA was extracted from the kanamycin-resistant transformant grown on the selection medium, and it was confirmed by southern hybridization that the kanamycin-resistant gene was inserted in orf3 gene and the orf3 gene was disrupted. Thus obtained transformant, *Gluconacetobacter intermedius* NCI 1051Δorf3 (hereinafter may be referred to as orf3-disrupted strain) was deposited under the Budapest Treaty on Feb. 28, 2007 with the International Patent Organism Depositary at the National Institute of Advanced Industrial Science and Technology (Central 6, 1-1 Higashi 1-Chome, Tsukuba-shi, Ibaraki-ken) under the Accession Number FERM BP-10792.

EXAMPLE 3

Foaming Suppressing Ability of the orf3-Disrupted Strain

The orf3-disrupted strain obtained in Example 2 in which the orf3 gene had been disrupted was compared to a wild-type strain for the foaming ability. Specifically, a shaking culture was carried out at 30° C. and 120 rpm in a medium (100 ml) containing 2% ethanol, 3% glucose, 0.5% yeast extract, 0.3% polypeptone, 100 μg/ml ampicillin, and 1% Celluclast 1.5 L (Novozymes) by using a Sakaguchi flask of 500 ml volume. The result demonstrated that foam formation was significantly suppressed in the orf3-disrupted strain as compared to the wild-type strain (FIG. 1). A complementary strain of orf3 was prepared to confirm this result. Consequently, it was confirmed that the phenotype was restored (FIG. 1).

EXAMPLE 4

Acetic Acid Fermentation Test for orf3-Disrupted Strain

The orf3-disrupted strain obtained in Example 2 in which the orf3 gene had been disrupted was compared to the wild-type strain for the foam formation and the production amount of acetic acid. Specifically, an aeration-agitation culture was carried out at 30° C., 500 rpm and 1 L/min in a medium (1.5 L) containing 3% ethanol, 3% glucose, 0.5% yeast extract, 0.3% polypeptone, 100 µg/ml ampicillin, 1% Celluclast 1.5 L (Novozymes) and 0.01% antifoaming agent by using a 3-liter mini-jar fermenter (Bioneer 300, 3 L; B.E. MARUBISHI Co. Ltd.). The ethanol concentration in the medium was controlled at 2% during fermentation. The aspect of foam formation is shown in FIG. 2 and fermentation results are shown in Table 1.

TABLE 1

|  | Wild-type strain | orf3-disrupted strain |
|---|---|---|
| Acetic acid concentration (weight/volume %) | 3.30 | 4.32 |

Figure 2:
FIG. 2 shows the aspect of foam formation when the wild-type strain and the orf3-disrupted strain were cultured.
Figure 2:
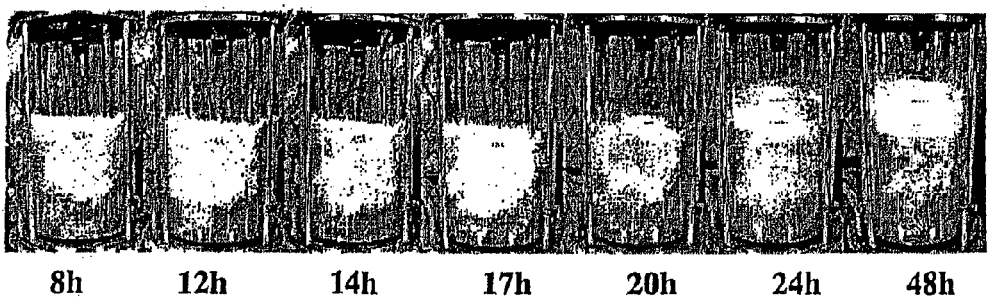

As is clear from FIG. 2, foam formation was significantly suppressed in the orf3-disrupted strain as compared to the wild-type strain. Further, as shown in Table 1, the acetic acid concentration in the culture broth was 4.32% for the orf3-disrupted strain as compared to 3.30% for the wild-type strain, and the production amount of acetic acid was increased by about 30%. These results demonstrated that foam formation during the culture was significantly suppressed by disrupting orf3 which encodes a protein involved in foam formation, and that vinegar containing a high concentration of acetic acid can be produced more efficiently.

INDUSTRIAL APPLICABILITY

According to the present invention, a gene involved in foam formation during culture of an acetic acid bacterium and a protein encoded by the gene are provided. Further provided is a method for significantly suppressing foam formation during culture by reducing or deleting the function of a protein encoded by the gene involved in foam formation during culture of an acetic acid bacterium. Therefore, a more efficient production of vinegar containing a high concentration of acetic acid is enabled by using an acetic acid bacterium with suppressed foam formation as a result of the above method.

---

The invention claimed is:

1. A method for producing an acetic acid bacterium with suppressed foaming ability, wherein said method comprises the step of modifying an endogenous gene in an acetic acid bacterium, wherein said modifying comprises the introduction of an inactivating deletion, insertion, substitution, or addition to the endogenous gene, wherein said endogenous gene encodes a protein involved in foam formation when said acetic acid bacterium is cultured, wherein said protein prior to said modifying is a protein selected from the group consisting of:
   (i) a protein that consists of the amino acid sequence of SEQ ID NO: 2;
   (ii) a protein that consists of an amino acid sequence which is a variant of the amino acid sequence of SEQ ID NO: 2, wherein said variant is the result of substituting, deleting, inserting or adding 1 to 20 amino acids in SEQ ID NO: 2, wherein said protein is involved in foam formation; and
   (iii) a protein which consists of an amino acid sequence that is at least 90% identical to the amino acid sequence of SEQ ID NO: 2, wherein said protein is involved in foam formation.

2. The method for producing an acetic acid bacterium with suppressed foaming ability according to claim 1, wherein the gene involved in foam formation of an acetic acid bacterium is a gene involved in the quorum-sensing system in an acetic acid bacterium.

3. A method for producing an acetic acid bacterium with suppressed foaming ability, wherein said method comprises the step of modifying an endogenous gene in an acetic acid bacterium, wherein said modifying comprises the introduction of an inactivating deletion, insertion, substitution, or addition to the endogenous gene, wherein said endogenous gene encodes a protein involved in foam formation when said acetic acid bacterium is cultured, wherein said endogenous gene prior to said modifying is a gene selected from the group consisting of:
   (i) a DNA which consists of the nucleotide sequence of SEQ ID NO: 1;
   (ii) a DNA which consists of a nucleotide sequence which is a variant of the nucleotide sequence of SEQ ID NO: 1, wherein said variant is the result of substituting, deleting, inserting or adding 1 to 20 nucleotides in SEQ ID NO: 1, wherein said DNA encodes a protein involved in foam formation;
   (iii) a DNA which consists of a nucleotide sequence that is at least 90% identical to the nucleotide sequence of SEQ ID NO: 1, wherein said DNA encodes a protein involved in foam formation;
   (iv) a DNA which encodes a protein that consists of the amino acid sequence of SEQ ID NO: 2;
   (v) a DNA which encodes a protein that consists of an amino acid sequence which is a variant of the amino acid sequence of SEQ ID NO: 2, wherein said variant is the result of substituting, deleting, inserting or adding 1 to 20 amino acids in SEQ ID NO: 2, wherein said protein is involved in foam formation; and
   (vi) a DNA which encodes a protein which consists of an amino acid sequence that is at least 90% identical to the amino acid sequence of SEQ ID NO: 2, wherein said protein is involved in foam formation.

* * * * *

SEQUENCE LISTING

<160> NUMBER OF SEQ ID NOS: 8

<210> SEQ ID NO 1
<211> LENGTH: 267
<212> TYPE: DNA
<213> ORGANISM: Gluconacetobacter intermedius

<400> SEQUENCE: 1

```
atgcggcctt ttgcaaacgg agaactcgct ctccatcgca gaaataatca tcaatatgga      60
aacagaaaaa taaaacacaa gaggaccaga actttgttct accgcgaagg agatatagaa     120
tacctagccc aaaaactatt ctctcagcac tatcccttc gaaagtggga cgaccgaccc       180
aattctatat cgggaggccc tacgcaagaa gaaaaagata aattcaagga tatcgcacgt     240
cagcaattat caggctggca cccggta                                           267
```

<210> SEQ ID NO 2
<211> LENGTH: 89
<212> TYPE: PRT
<213> ORGANISM: Gluconacetobacter intermedius

<400> SEQUENCE: 2

```
Met Arg Pro Phe Ala Asn Gly Glu Leu Ala Leu His Arg Arg Asn Asn
1               5                   10                  15

His Gln Tyr Gly Asn Arg Lys Ile Lys His Lys Arg Thr Arg Thr Leu
            20                  25                  30

Phe Tyr Arg Glu Gly Asp Ile Glu Tyr Leu Ala Gln Lys Leu Phe Ser
        35                  40                  45

Gln His Tyr Pro Phe Arg Lys Trp Asp Asp Arg Pro Asn Ser Ile Ser
    50                  55                  60

Gly Gly Pro Thr Gln Glu Glu Lys Asp Lys Phe Lys Asp Ile Ala Arg
65                  70                  75                  80

Gln Gln Leu Ser Gly Trp His Pro Val
```

```
<210> SEQ ID NO 3
<211> LENGTH: 29
<212> TYPE: DNA
<213> ORGANISM: Artificial Sequence
<220> FEATURE:
<223> OTHER INFORMATION: Primer 1

<400> SEQUENCE: 3
ccggaattcg gatatgtcgc tccccattc                                    29

<210> SEQ ID NO 4
<211> LENGTH: 31
<212> TYPE: DNA
<213> ORGANISM: Artificial Sequence
<220> FEATURE:
<223> OTHER INFORMATION: Primer 2

<400> SEQUENCE: 4
gcgggtaccc tgcgatggag agcgagttct c                                 31

<210> SEQ ID NO 5
<211> LENGTH: 29
<212> TYPE: DNA
<213> ORGANISM: Artificial Sequence
<220> FEATURE:
<223> OTHER INFORMATION: Primer 3

<400> SEQUENCE: 5
ggcaagcttg caattatcag gctggcacc                                    29

<210> SEQ ID NO 6
<211> LENGTH: 29
<212> TYPE: DNA
<213> ORGANISM: Artificial Sequence
<220> FEATURE:
<223> OTHER INFORMATION: Primer 4

<400> SEQUENCE: 6
gccaagctta ccaggtgcgt gagggcatg                                    29

<210> SEQ ID NO 7
<211> LENGTH: 29
<212> TYPE: DNA
<213> ORGANISM: Artificial Sequence
<220> FEATURE:
<223> OTHER INFORMATION: Primer 5

<400> SEQUENCE: 7
ccgcccggga agcttcacgc tgccgcaag                                    29

<210> SEQ ID NO 8
<211> LENGTH: 20
<212> TYPE: DNA
<213> ORGANISM: Artificial Sequence
<220> FEATURE:
<223> OTHER INFORMATION: Primer 6

<400> SEQUENCE: 8
gagcccgggg tgggcgaaga                                              20
```